(12) United States Patent
Buysse

(10) Patent No.: US 8,192,427 B2
(45) Date of Patent: Jun. 5, 2012

(54) SURFACE ABLATION PROCESS WITH ELECTRODE COOLING METHODS

(75) Inventor: Steven P. Buysse, Longmont, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 808 days.

(21) Appl. No.: 12/135,425

(22) Filed: Jun. 9, 2008

(65) Prior Publication Data

US 2009/0306659 A1 Dec. 10, 2009

(51) Int. Cl.
*A61B 18/12* (2006.01)

(52) U.S. Cl. .............................. 606/41; 606/49; 606/50

(58) Field of Classification Search .................... 606/41, 606/49, 50
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,532,924 A * | 8/1985 | Auth et al. | 606/50 |
| 4,572,190 A | 2/1986 | Azam et al. | |
| 4,709,698 A | 12/1987 | Johnston et al. | |
| 4,798,215 A | 1/1989 | Turner | |
| 4,862,890 A * | 9/1989 | Stasz et al. | 606/48 |
| 5,097,844 A | 3/1992 | Turner | |
| 5,201,900 A | 4/1993 | Nardella | |
| 5,417,210 A | 5/1995 | Funda et al. | |
| 5,647,871 A * | 7/1997 | Levine et al. | 606/45 |
| 5,827,271 A | 10/1998 | Buysse et al. | |
| 6,031,375 A | 2/2000 | Atalar et al. | |
| 6,068,629 A * | 5/2000 | Haissaguerre et al. | 606/41 |
| 6,071,281 A | 6/2000 | Burnside et al. | |
| 6,322,584 B2 * | 11/2001 | Ingle et al. | 607/96 |
| 6,375,606 B1 | 4/2002 | Garibaldi et al. | |
| 6,432,104 B1 * | 8/2002 | Durgin et al. | 606/45 |
| 6,603,994 B2 | 8/2003 | Wallace et al. | |
| 6,692,489 B1 | 2/2004 | Heim et al. | |
| 6,725,080 B2 | 4/2004 | Melkent et al. | |
| 6,786,905 B2 | 9/2004 | Swanson et al. | |
| 6,939,348 B2 | 9/2005 | Malecki et al. | |

(Continued)

FOREIGN PATENT DOCUMENTS

DE 390937 3/1924

(Continued)

OTHER PUBLICATIONS

U.S. Appl. No. 08/483,742, filed Jun. 7, 1995.

(Continued)

*Primary Examiner* — Michael Peffley
*Assistant Examiner* — Daniel Fowler

(57) ABSTRACT

A bipolar electrode assembly includes a substrate having proximal and distal ends and supports first electrode and second electrodes. The first and second electrodes are disposed in an interwoven configuration across the surface of the substrate from the proximal to distal ends. A cooling medium is disposed interposed between the first and second electrodes from the proximal to distal ends. The first and second electrodes each include a plurality of finger-like prongs which either extend lengthwise or transversely or the first and second electrodes extend spiral inwardly along the surface of the substrate. The prongs of the first electrode intermesh with the prongs of the second electrode. Each prong is separated by the cooling medium. First and second electrodes may be disposed in a lengthwise alternating configuration across the surface of the substrate with a cooling medium disposed in vertical registration thereunder.

14 Claims, 8 Drawing Sheets

U.S. PATENT DOCUMENTS

| | | |
|---|---|---|
| 7,169,145 B2 | 1/2007 | Isaacson et al. |
| 7,175,621 B2 | 2/2007 | Heim et al. |
| 7,186,251 B2 | 3/2007 | Malecki et al. |
| 7,229,437 B2 | 6/2007 | Johnson et al. |
| 7,234,225 B2 | 6/2007 | Johnson et al. |
| 7,235,070 B2 | 6/2007 | Vanney |
| 7,293,562 B2 | 11/2007 | Malecki et al. |
| 7,367,975 B2 | 5/2008 | Malecki et al. |
| 7,439,736 B2 | 10/2008 | Meaney et al. |
| 7,467,015 B2 | 12/2008 | Van der Weide |
| 7,565,207 B2 | 7/2009 | Turner et al. |
| 2002/0022836 A1 | 2/2002 | Goble et al. |
| 2004/0097805 A1 | 5/2004 | Verard et al. |
| 2004/0242992 A1 | 12/2004 | Hareyama |
| 2006/0009759 A1* | 1/2006 | Chrisitian et al. .............. 606/41 |
| 2006/0106375 A1 | 5/2006 | Werneth et al. |
| 2007/0208334 A1 | 9/2007 | Woloszko et al. |
| 2007/0208335 A1 | 9/2007 | Woloszko et al. |
| 2007/0250055 A1 | 10/2007 | Johnson et al. |
| 2007/0250056 A1 | 10/2007 | Vanney |
| 2007/0287999 A1 | 12/2007 | Malecki et al. |
| 2007/0299434 A1 | 12/2007 | Malecki et al. |
| 2008/0004618 A1 | 1/2008 | Johnson et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 050 279 | 4/2000 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/016119 | 2/2005 |

OTHER PUBLICATIONS

U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.

U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.

Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111; (1984), pp. 2490-2499.
Crawford et al., "Use of the LigaSure™ Vessel Sealing System in Urologic Cancer Surger" Grand Rounds In Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, " LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thetmoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
S. Humphries Jr. et al., "Finite•Element Codes to Model Electrical Heating and Non•Llnear Thermal Transport in Biological Media", Proc. ASME HTD-355, 131 (1997).
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.

European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

SURFACE ABLATION PROCESS WITH ELECTRODE COOLING METHODS

BACKGROUND

1. Technical Field

The present disclosure relates to electrode assemblies configured to be applied to electrosurgical instruments used for open and endoscopic surgical procedures for coagulation or ablating tissue.

2. Related Prior Art

In procedures involving treatment of biological tissue, it may be desirable to thermally treat an exposed tissue surface. A surface ablation device may be configured to conform to many different surfaces and tissue structures making it applicable for a wide range of clinical procedures and target tissue sites. A few examples are liver resection in order to stop surface bleeding or to increase resection margin; spleen ablation to prevent bleeding to a lacerated spleen; endometrium ablation to reduce uterine bleeding; sternum ablation to reduce bleeding of bone after separation of the sternum; parasinoidal ablation to reduce bleeding during an ear, nose and throat (ENT) procedure; and sacrum ablation to reduce bleeding during a lower anterior bowel resection. The method of using such surface ablation device is commonly referred to as contact desiccation, surface coagulation or ablation.

Electrosurgical coagulation is typically referred to as the application of radio-frequency (RF) energy, microwave (MW), and ultrasound (US). Often, such coagulation is achieved with monopolar energy arcing to tissue resulting in non-contact coagulation. The process of covering a large surface is commonly referred to as "painting", i.e., painting the surface by applying arcs resulting in a coagulated surface.

Electrosurgical desiccation is typically referred to as the application of RF energy for the purpose of stopping bleeding. Coagulation is often achieved with bipolar or monopolar energy with the electrode(s) in direct contact with the tissue. Such a process results in contact desiccation or dehydration of the tissue. One process achieving a similar effect is often referred to in the art as "buzzing the hemostat" using monopolar energy. Another process achieving similar effect is tissue fusion using bipolar energy.

Ablation is often referred to as the application of energy as a therapeutic treatment or to thermally damage cellular structures. Ablation is typically achieved with RF, MW, US or cryogenic energy with the respective applicators in direct contact with the tissue.

SUMMARY

The present disclosure relates to an ablation assembly designed and configured to enhance thermal treatment of a consistent volume of patient tissue. The thermal treatment may include desiccation, coagulation and ablation during which the electrodes of the electrode assembly are cooled. The present disclosure relates also to a surface ablation system configured for thermal treatment of tissue that results in a reduction in tissue build-up on the electrode surfaces and more efficient application of energy. Such efficient application of energy provides contact desiccation (surface ablation) of tissue with minimal tissue sticking and charring of the electrode surfaces. Cooling of the electrode assembly allows deeper thermal penetration by reducing rapid heating and rise of impedance at the electrode to tissue interface by cooling the electrodes, thereby cooling the surfaces of the electrodes in contact with tissue.

In view of the foregoing, the present disclosure relates to a bipolar electrode assembly that includes a substrate having proximal and distal ends and supporting first electrode and second electrodes that are each adapted to connect to alternate potentials of an electrosurgical energy source. The first and second electrodes are disposed in an interwoven configuration across the surface of the substrate from the proximal to distal ends thereof. A cooling medium is disposed interposed between the first and second electrodes from the proximal to distal ends of the substrate. The cooling medium may be disposed at least partially recessed within the substrate. The cooling medium may also be disposed atop the substrate.

In one embodiment according to the present disclosure, the first and second electrodes each include a plurality of finger-like prongs which extend lengthwise along the surface of the substrate. The prongs of the first electrode intermesh with the prongs of the second electrode. Each prong is separated by a cooling medium.

In another embodiment, the first and second electrodes each include a plurality of finger-like prongs which extend transversely across the surface of the substrate from the proximal to distal ends thereof. The prongs of the first electrode intermesh with the prongs of the second electrode, and each prong is separated by a cooling medium.

In still another embodiment, the first and second electrodes are arranged atop the substrate to extend from the proximal to distal ends of the substrate and spiral inwardly with the cooling medium disposed therebetween. The cooling medium may be dispersed through a conduit recessed within the substrate or, alternatively, the cooling medium may also be dispersed through a conduit disposed atop the substrate. Still further, the cooling medium may be dispersed in a cooling conduit disposed in a serpentine configuration in the space formed between the first electrode and the second electrode.

The substrate may be selected from the group consisting of plastic or ceramic, such as acrylonitrile butadiene styrene (ABS), polyethylene, polypropylene, zirconium oxide also referred to as zirconia, barium titanate, Sialons (silicon aluminum oxynitride), a cool polymer material, or similar suitable electrically insulative material. The cooling medium may be selected from the group consisting of saline, water, alcohol, glycine, oil, or other suitable cooling medium.

In still another embodiment according to the present disclosure, the bipolar electrode assembly includes a substrate having proximal and distal ends and supporting a plurality of first electrodes and a plurality of second electrodes. Each electrode is adapted to connect to alternate potentials of an electrosurgical energy source. The plurality of first and second electrodes are disposed in a lengthwise alternating configuration across the surface of the substrate, and a cooling medium is disposed in vertical registration under each of the plurality of first and second electrodes. The cooling medium may be dispersed in a single conduit which snakes lengthwise across the width of the substrate in vertical registration with each of the plurality of electrodes. Alternatively, a first cooling medium may be dispersed in a first conduit which snakes lengthwise across the width of the substrate in vertical registration with the plurality of first electrodes and a second cooling medium may be dispersed in a second conduit which snakes lengthwise across the width of the substrate in vertical registration with the plurality of second electrodes. The first conduit and the second conduit may at least partially overlap each other.

In still another embodiment, the cooling medium is dispersed in a single conduit which is distributed lengthwise across the width of the substrate in vertical registration with each of the plurality of electrodes.

BRIEF DESCRIPTION OF THE DRAWINGS

Various embodiments of the subject instrument are described herein with reference to the drawings wherein.

DETAILED DESCRIPTION

The present disclosure relates to an electrode assembly designed to thermally treat a consistent volume of patient tissue. The thermal treatment includes desiccation, coagulation and ablation during which the electrodes of the electrode assembly are cooled. The present disclosure relates also to a surface ablation system for thermal treatment of tissue that results in a reduction in tissue build-up on the electrode surfaces and more efficient application of energy. Such efficient application of energy provides contact desiccation (surface ablation) of tissue with minimal tissue sticking and charring of the electrode surfaces. Cooling of the electrode assembly allows deeper thermal penetration by reducing rapid heating and rise of impedance at the electrode to tissue interface by cooling the electrodes, thereby cooling the surfaces of the electrodes in contact with tissue.

The electrode assemblies according to the present disclosure enable treating of biological tissue by causing a uniform volume of tissue necrosis along an exposed surface of tissue. The electrode assemblies enable thermal treatment of the tissue to increase the clinical margin at the edge of a lesion or to reduce bleeding over a large surface area.

In addition to the effects of efficient cooling of the electrode assemblies, it has been found that by providing a thermally conductive and electrically non-conductive material adjacent to the electrically conductive ablating surfaces, surgeons can more readily and more easily produce a consistent, high quality tissue treatment and effectively reduce thermal spread across or to adjacent tissue. For the purposes herein the term "thermal spread" refers generally to the heat transfer (heat conduction, heat convection or electrical current dissipation) dissipating along the periphery of the electrically conductive or electrically active surfaces to adjacent tissue. This can also be termed "collateral damage" to adjacent tissue and is further discussed in commonly owned, co-pending PCT Patent Application PCT/US04/13273 by Chapman et al., filed on Apr. 29, 2004, entitled "ELECTROSURGICAL INSTRUMENT WHICH REDUCES THERMAL DAMAGE TO ADJACENT TISSUE", published as WO 2004/098383 A2 on Nov. 18, 2004.

Figure 1A:
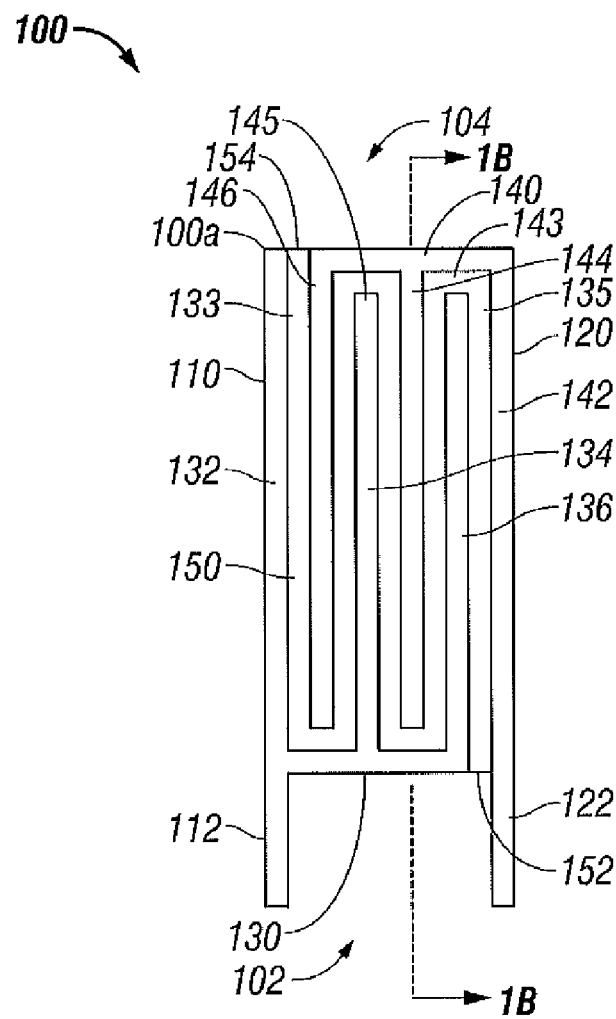
FIG. 1A is a plan view of a bipolar electrode assembly having a linear interwoven configuration according to the present disclosure.

Referring now to FIGS. 1A, 1B, 2A, 2B, 3A, 3B, specifically FIG. 1A illustrates an exemplary embodiment of a bipolar (i.e., alternating polarity) electrode assembly having a linear interwoven configuration according to the present disclosure. More particularly, electrode assembly 100 includes a first electrode 110 and a second electrode 120 that are each configured having first and second power supply contact extensions 112 and 122, respectively. The power supply contact extensions 112 and 122 may be electrically coupled to an electrosurgical generator (not shown). For reference purposes, the proximal end 102 of the electrode assembly 100 is defined as an end of the electrode assembly 100 at which the contact extensions 112 and 122 are disposed. The distal end 104 of the electrode assembly 100 is defined as the end of the electrode assembly 100 distal to the proximal end 102.

In one embodiment, the first and second power supply contact extensions 112 and 122 are each configured as linear strips of conductive foil material, e.g., stainless steel foil or other suitable conductive foils such as may be known in the art. The first and second electrodes 110 and 120, respectively, are each configured in a comb-like or fork-like arrangement wherein a base member 130 projects orthogonally and proximally from one side of first contact extension 112 and a base member 140 projects orthogonally and distally from one side of second contact extension 122.

The first contact extension 112 may be integrally formed as a first prong 132 extending distally from the base member 130 while a second prong 134 and a third prong 136 each extend distally from base member 130 wherein the first, second and third prongs 132, 134, and 136, respectively, are each parallel to one another to provide a substantially E-shaped configuration to the first electrode 110 such that the E-shaped configuration extends distally outward from the base member 130. The first prong 132 and the second prong 134 thereby form a space 133 therebetween while the second prong 134 and the third prong 136 thereby form a space 135 therebetween.

In contrast, the second contact extension 122 may be integrally formed with a first prong 142 while a second prong 144 and a third prong 146 each extend proximally from base member 140 wherein the first, second and third prongs 142, 144, and 146 are each parallel to one another to provide a substantially E-shaped configuration to the second electrode 120 such that the E-shaped configuration extends proximally inward from the base member 140. In a similar manner as with respect to the first electrode 110, the first prong 142 and the second prong 144 thereby form a space 143 therebetween while the second prong 144 and the third prong 146 thereby form a space 145 therebetween.

Those skilled in the art will recognize that, and understand how, the electrodes 110 and 120 may be configured with a greater or lesser number of prongs. In a similar manner as with respect to the contact extensions 112 and 122, the electrodes 110 and 120 may be each configured as linear strips of conductive foil material. Alternatively, the electrodes 110 and 120 may be of a rigid or flexible tubular configuration and made from, for example but not limited to, stainless steel tubing having insulated sections to protect tissue to be left untreated. Alternatively, the electrodes 110 and 120 may be of a rigid or flexible tubular configuration and made from electrically non-conductive, thermally conductive polymer material with an electrically conductive material surrounding the non-conductive tubular member. The electrically conductive material may be conductive foil placed over a tubular electrode, or the electrically conductive material may be vapor deposited on the tubular electrode. A cooling fluid may thermally cool the tissue contacting electrode by internal passage of the cooling fluid through the tubular conduit. Tubular electrodes provide a rounded configuration that reduce high current densities that are caused by high electric fields that otherwise occur at the sharp edges of flat surface electrodes.

The distally outward E-shaped configuration of first electrode 110 and the proximally inward E-shaped configuration of second electrode 120 enable the second prong 134 of first electrode 110 to be disposed within the space 145 between the second prong 144 and the third prong 146 of the second electrode 120 while at the same time enabling the third prong 136 of the first electrode 110 to be disposed within the space 143 between the first prong 142 and the second prong 144 of the second electrode assembly 120. Thus, the space 133 between the first prong 132 and the second prong 134 of the first electrode 110 at least partially overlaps the space 145 between the second prong 144 and the third prong 146 of the second electrode 120 while the space 135 between the second prong 134 and the third prong 136 of the first electrode 110 at least partially overlaps the space 143 between the first prong 142 and the second prong 144 of the second electrode 120.

Figure 1B:
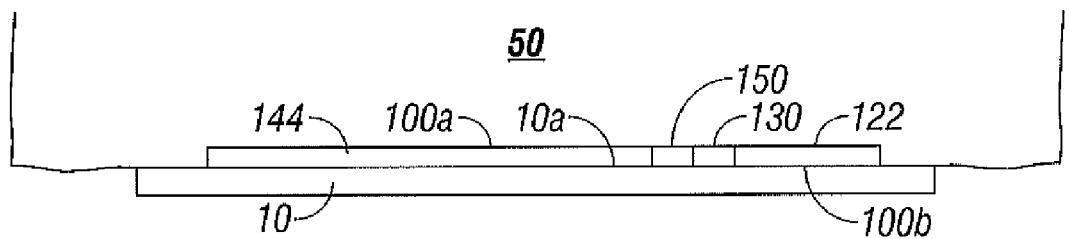
FIG. 1B is a cross-sectional view of the bipolar electrode assembly of FIG. 1A.

The resulting interwoven configuration of the first and second electrodes 110 and 120, respectively, enables the first and second electrodes 110 and 120, respectively, to be disposed without contact between each other to maintain electrical isolation therebetween (see FIG. 1B). The partially overlapping spaces 133 and 145 and 135 and 143 enable a cooling conduit 150 to be disposed therein in a serpentine configuration between the first and second electrodes 110 and 120, respectively. The cooling conduit 150 includes a proximal inlet port 152 for receiving a cooling medium, e.g., saline, water, alcohol, glycine, oil, gel or other suitable medium and a distal outlet port 154 for discharging the cooling medium.

As defined herein, a cooling medium may also include a solid material such as, for example, but not limited to a thermally conductive material that is also electrically non-conductive. Such thermally conductive materials are made from a material having a high thermal conductivity value or "k" value and minimum electrical conductively, e.g., anodized aluminum. Alternatively, an exemplary thermally conductive material may be made from or combined with a semi-resilient or elastomeric material so as not to inflict mechanical damage to the tissue during compression. Mechanical damage may also be diminished by minimizing the overall tissue contact area of the thermally conductive material.

Other examples of thermally conductive and electrically non-conductive materials which can be utilized to minimize thermal damage to surrounding tissue include, but are not limited to, thermally conductive plastic materials which dissipate heat along a preferred isothermal profile to the surrounding environment resulting in a lower maximum temperature and reduced formation of hot spots. Examples of such materials are commonly sold under the trademark CoolPoly® by Cool Polymers, Inc., of Rhode Island and composite materials such as $ALO_2$. As also defined herein, a cooling medium may include a thermoelectric material.

As illustrated in FIG. 1B, the first and second electrodes 110 and 120, respectively, and the cooling conduit 150 may be disposed on a substrate 10 and maintain electrical isolation between the opposite polarity electrodes 110 and 120.

As illustrated in FIGS. 1A and 1B, the resulting interwoven configuration of the first and second electrodes 110 and 120, respectively, results in electrode assembly 100 being formed in a thin generally rectangular configuration having a first substantially planar side 100a and a second substantially planar side 100b, disposed on the substrate 10 in interfacing relationship therewith, wherein the first substantially planar side 100a is disposed in contact with patient tissue 50 during a surface ablation process. The interwoven configuration of the electrodes 110 and 120 and the cooling conduit 150 disposed between the prongs 132, 134, 136 and 142, 144, 146 enable efficient cooling of the surface of the tissue 50 during the ablation process.

In the example shown in FIGS. 1A and 1B, in one embodiment, a cooling medium such as a thermally conductive and electrically non-conductive material (not shown) may be disposed in contact with the substrate 10 to provide or enhance heat transfer from the electrode assembly 100.

Figure 2A:
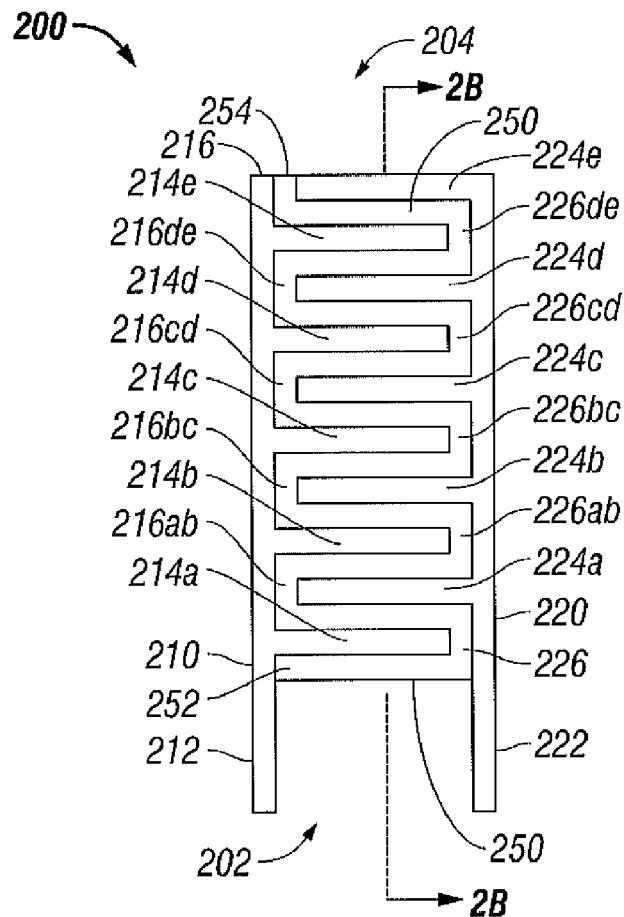
FIG. 2A is a plan view of a bipolar electrode assembly having a transverse interwoven configuration according to the present disclosure.

FIG. 2A illustrates another exemplary embodiment of a bipolar (i.e., alternating polarity) electrode assembly according to the present disclosure. Electrode assembly 200 is generally similar to the aforementioned electrode assembly 100 except that electrode assembly 200 has a transverse interwoven configuration rather than a linear interwoven configuration. More particularly, electrode assembly 200 includes a first electrode 210 and a second electrode 220 that are each configured as also having first and second power supply contact extensions 212 and 222, respectively. For reference purposes, the proximal end 202 of the electrode assembly 200 is defined as an end of the electrode assembly 200 at which the contact extensions 212 and 222 are disposed. The distal end 204 of the electrode assembly 200 is defined as the end of the electrode assembly 200 distal to the proximal end 202.

In one embodiment, similar to electrode assembly 100, the first and second power supply contact extensions 212 and 222 are each configured as linear strips of conductive material, e.g., stainless steel foil in a similar manner as described above for contact extensions 112 and 122. The first and second contact extensions 212 and 222 extend from the proximal end 202 to the distal end 204. The first and second electrodes 210 and 220, respectively, again are each configured in a comb-like or fork-like arrangement. However, instead of base members 130, 140 projecting orthogonally and proximally from one side of first and second contact extension 112, 122, respectively, a plurality of prongs, e.g., first through fifth prongs 214a through 214e, extend transversely and orthogonally from one side of the first contact extension 212 to form electrode 210 while a plurality of prongs, e.g., first through fifth prongs 224a through 224e, extend transversely and in one embodiment orthogonally from one side of second contact extension 222 to form electrode 220.

In a similar manner, the first through fifth prongs 214a through 214e being integrally formed with, orthogonal to, and extending transversely from, one side of the first contact extension 212 thus provide a substantially E-shaped configuration to the first electrode 210.

At least the first and second prongs 214a and 214b, respectively, of the first electrode 210 form a space 216ab therebetween, and at least the first and second prongs 224a and 224b, respectively, of the second electrode 220 form a space 226ab therebetween. Additionally, second and third prongs 214b and 214c, respectively, of the first electrode 210 form a space 216bc, therebetween, and second and third prongs 224b and 224c, respectively, of the second electrode 220 form a space 226bc, therebetween. Third and fourth prongs 214c and 214d, respectively, of the first electrode 210 form a space 216cd, therebetween, and third and fourth prongs 224c and 224d, respectively, of the second electrode 220 form a space 226cd, therebetween. Fourth and fifth prongs 214d and 214e, respectively, of the first electrode 210 also form a space 216de, therebetween, and fourth and fifth prongs 224d and 224e, respectively, of the second electrode 220 form a space 226de, therebetween.

In a similar manner, the electrode assembly 200 is configured wherein the first prong 224a of the second electrode 220 is disposed in the space 216ab formed between first and second prongs 214a and 214b, respectively, of the first electrode 210. The first prong 214a of the first electrode 210 is disposed in a space 226 adjacent to the first prong 224a of the second electrode 220. The second prong 224b of the second electrode 220 is disposed in the space 216bc formed between the second and third prongs 214b and 214c, respectively, of the first electrode 210 and the second prong 214b of the first electrode 210 is disposed in the space 226ab between the first and second prongs 224a and 224b, respectively, of the second electrode 220. The third prong 224c of the second electrode 220 is disposed in the space 216cd formed between the third and fourth prongs 214c and 214d, respectively, of the first electrode 210 and the third prong 214c of the first electrode 210 is disposed in the space 226bc formed between the second and third prongs 226b and 226c, respectively, of the second electrode 220.

Additionally, the fourth prong 224d of the second electrode 220 is disposed in the space 216de formed between the fourth and fifth prongs 214d and 214e, respectively, of the first electrode 210 while the fourth prong 214d of the first electrode 210 is disposed in the space 226cd formed between the third and fourth prongs 226c and 226d, respectively, of the second electrode 220. The fifth prong 224e of the second electrode 220 is disposed in a space 216 adjacent to the fifth prong 214e of the first electrode 210 while the fifth prong 214e of the first electrode 210 is disposed in the space 226de formed between the fourth and fifth prongs 226d and 226e, respectively, of the second electrode 220.

The first through fifth prongs 214a, 214b, 214c, 214d and 214e, respectively, of the first electrode 210 are disposed in their respective spaces 226, 226ab, 226bc, 226cd and 226de without contacting the second electrode 220. The first through fifth prongs 224a, 224b, 224c, 224d and 224e, respectively, of the second electrode 220 are disposed in their respective spaces, 216ab, 216bc, 216cd, 216de and 216 without contacting the first electrode 210. In this arrangement, the first and second electrodes 210 and 220, respectively, form thereby a transverse interwoven or interlocking configuration maintaining electrical isolation between the first and second electrodes 210 and 220, respectively.

In a similar manner, spaces 226, 226ab, 226bc, 226cd and 226de at least partially overlap, respectively, spaces 216ab, 216bc, 216cd, 216de and 216. A cooling conduit 250 is disposed in a serpentine configuration in spaces 216ab, 216bc, 216cd, 216de and 216 and spaces 226, 226ab, 226bc, 226cd and 226de.

Thus, in a similar manner, the resulting interwoven configuration of the first and second electrodes 210 and 220, respectively, enables the first and second electrodes 210 and 220, respectively, to be disposed without contact between each other to maintain electrical isolation therebetween. The partially overlapping spaces 216ab and 226; 216bc and 226ab; 216cd and 226bc; 216de and 226cd enable a cooling conduit 250 to be disposed therein in a serpentine configuration between the first and second electrodes 210 and 220, respectively. The cooling conduit 250 includes a proximal inlet port 252 for receiving a cooling medium, e.g., a suitable sterile solution such as water, saline and the like, and a distal outlet port 254 for discharging the cooling medium. Other cooling elements such as the above identified dielectrics and polymers are also envisioned.

Figure 2B:
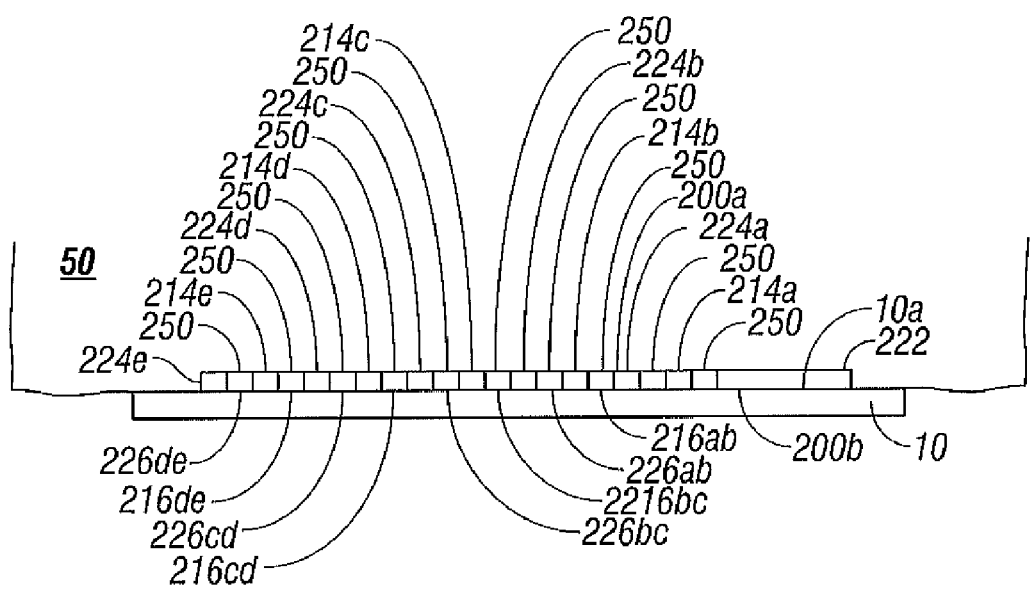
FIG. 2B is a cross-sectional view of the bipolar electrode assembly of FIG. 2A.

As illustrated in FIG. 2B, the first and second electrodes 210 and 220, respectively, and the cooling conduit 250 may be disposed on substrate 10 and maintain electrical isolation between the opposite polarity electrodes 210 and 220.

As illustrated in FIGS. 2A and 2B, in a similar manner as described above with respect to electrode assembly 100, the resulting interwoven configuration of the first and second electrodes 210 and 220, respectively, results in electrode assembly 200 to be formed in a thin generally rectangular configuration having a first substantially planar side 200a and a second substantially planar side 200b, disposed on the substrate 10 in interfacing relationship therewith, wherein the first substantially planar side 100a is disposed in contact with patient tissue 50 during a surface ablation process. The interwoven configuration of the electrodes 210 and 220 and the cooling conduit 250 disposed between the prongs 214a through 214e and 224a through 224e enable efficient cooling of the surface of the tissue 50 during the ablation process.

Figure 3A:
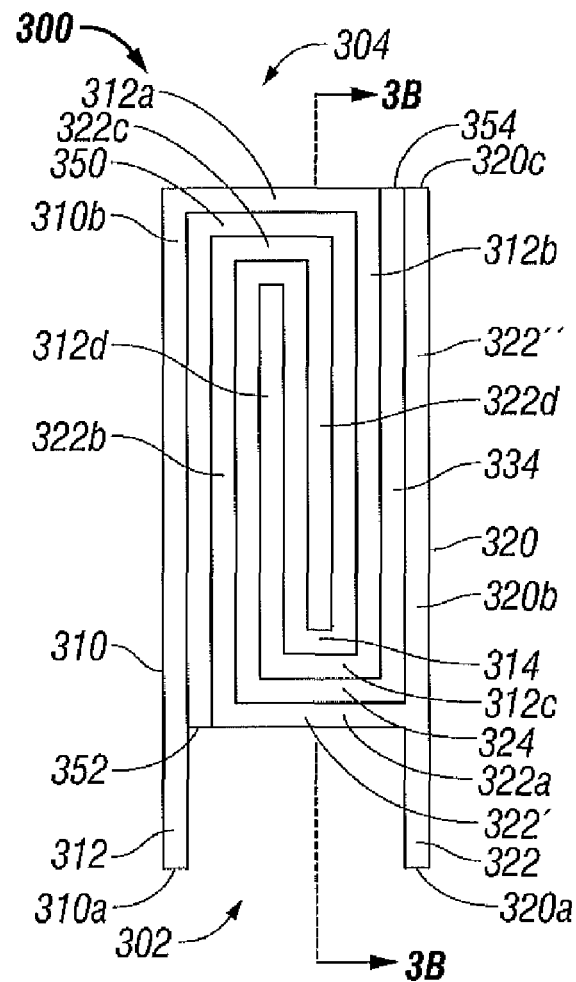
FIG. 3A is a plan view of a bipolar electrode assembly having an interlocking spiral configuration according to the present disclosure.

FIG. 3A illustrates still another exemplary embodiment of a bipolar (i.e., alternating polarity) electrode assembly according to the present disclosure. Electrode assembly 300 is similar to the aforementioned electrode assemblies 100 and 200 except that electrode assembly 300 has a spiral interwoven configuration rather than a linear interwoven configuration or a transverse interwoven configuration. More particularly, electrode assembly 300 includes a first electrode 310 and a second electrode 320 that are each configured as also having first and second power supply contact extensions 312 and 322, respectively. For reference purposes, the proximal end 302 of the electrode assembly 300 is defined as an end of the electrode assembly 300 at which the contact extensions 312 and 322 are disposed. The distal end 304 of the electrode assembly 300 is defined as the end of the electrode assembly 300 distal to the proximal end 302.

In one embodiment, in a similar manner as with respect to electrode assemblies 100 and 200, first and second power supply contact extensions 312 and 322 are each configured as linear strips of conductive material, as described above with respect to contact extensions 112, 122 and 212, 222. The electrodes 310 and 320 may be integrally formed with the respective power supply contact extensions 312 and 322 and may be made from the same material as the contact extensions 312 and 322.

The first and second contact extensions 312 and 322 extend from proximal tips 310a and 320a at the proximal end 302. In one embodiment, the first electrode 310 is configured to extend from the proximal tip 310a contact extension 312 at the proximal end 302 as a prong in a clockwise inward rectangular spiral arrangement. More particularly, the first electrode 310 extends as a prong in an inward spiral arrangement. At the distal end 304, a first extension leg 312a extends transversely and clockwise from a side of the contact extension 312. A second extension leg 312b extends transversely and clockwise from a side at the end of the first extension leg 312a, while a third extension leg 312c extends transversely from a side at the end of the second extension leg 312c, such that second extension leg 312b is parallel to the first contact extension 312. A fourth extension leg 312d extends transversely and clockwise from a side at the end of the third extension leg 312c to a distal tip 310b such that the fourth extension leg 312d is parallel to the second extension leg 312c, while the third extension leg 312c is parallel to the first extension leg 312a. Thus, the contact extension 312 of the first electrode 310 extending as a prong in an inward spiral arrangement forms a space 314 extending spirally between and around the contact extension 312 and the various extension legs 312a to 312d.

The second electrode 310 is configured similarly to extend from the proximal tip 320a of contact extension 322 at the proximal end 302 as a prong in a clockwise inward rectangular spiral arrangement. However, second electrode 320 differs from first electrode 310 in that second electrode 320 includes a first prong 322' having a first extension leg 322a that extends transversely from a side of the second contact extension 322 at point 324 thereon that is near the proximal end 302, ultimately terminating at a first distal tip 320b, after following a spiral path. The second contact extension 322 extends linearly as a second prong 322" that terminates at a second distal tip 320c that extends to the distal end 304 of the electrode assembly 300.

The first prong 322' further includes a second extension leg 322b that extends transversely and clockwise from a side of the first extension leg 322a such that the second extension leg 322b is parallel to the second prong 322". A third extension leg 322c then extends transversely and clockwise from a side of the second extension leg 322b and a fourth extension leg 322d extends transversely and clockwise from a side of the third extension leg 322c to terminate at the first distal tip 320b such that the fourth extension leg 322d is parallel to both the second prong 322" and the second extension leg 322c, while the third extension leg 322c is parallel to the first extension leg 322a. Again, in a similar manner, the contact extension 322 of the second electrode 320 extending as first prong 322' in an inward spiral arrangement, in conjunction with second prong 322" extending linearly to the second distal tip 320c forms a space 334 extending spirally between and around the second prong 322" and the various extension legs 322a to 322d of the first prong 322'.

The contact extension 322 of the second electrode 320, extending as first and second prongs 322' and 322", respectively, is disposed in space 314 formed between the contact extension 312 of the first electrode 310, extending as a prong in an inward spiral arrangement, without contacting the first electrode 310. Vice versa, the contact extension 312 of the first electrode 310, extending as a prong, is disposed in the space 334 formed between the contact extension 322 of the second electrode 320 without contacting the second electrode 320. Thus, the first and second electrodes 310 and 320, respectively, form thereby a spiral interwoven or interlocking configuration maintaining electrical isolation between each other.

The space 314 formed between the contact extension 312 of the first electrode 310 at least partially overlaps the space 334 formed between the contact extension 322 of the second electrode 320. In a similar manner as described above with respect to electrode assemblies 100 and 200, a cooling conduit 350 is disposed in a serpentine configuration in the spaces 314 and 334 that at least partially overlap each other. The cooling conduit 350 includes a proximal inlet port 352 for receiving a cooling medium, e.g., a suitable sterile solution such as water, saline, and the like and a distal outlet port 354 for discharging the cooling medium. Again, other cooling elements such as the above identified dielectrics and polymers are also envisioned.

Figure 3B:
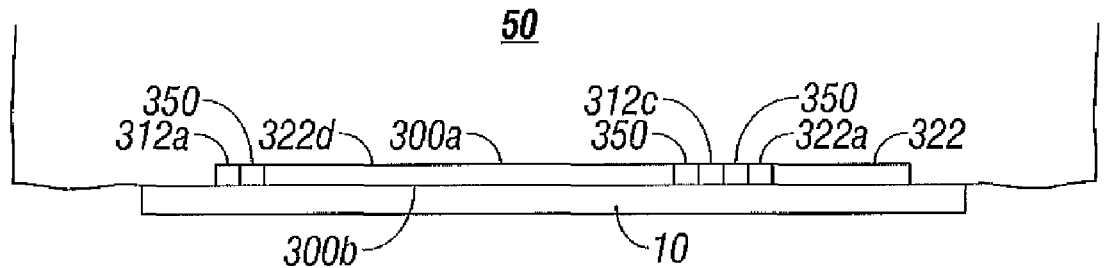
FIG. 3B is a cross-sectional view of the bipolar electrode assembly of FIG. 3A.

As illustrated in FIG. 3B, the first and second electrodes 310 and 320, respectively, and the cooling conduit 350 may be disposed on a substrate 10 and maintain electrical isolation between the opposite polarity electrodes 310 and 320.

In a similar manner as described above with respect to electrode assemblies 100 and 200, the resulting interwoven configuration of the first and second electrodes 310 and 320, respectively, enables electrode assembly 300 to be formed in a thin generally rectangular configuration having a first substantially planar side 300a and a second substantially planar side 300b, disposed on the substrate 10 in interfacing relationship therewith, wherein the first substantially planar side 300a is disposed in contact with patient tissue 50 during a surface ablation process. The interwoven configuration of the electrodes 310 and 320 and the cooling conduit 350 disposed between the prongs 322' and 322" also enable efficient cooling of the surface of the tissue 50 during the ablation process.

Figure 3C:
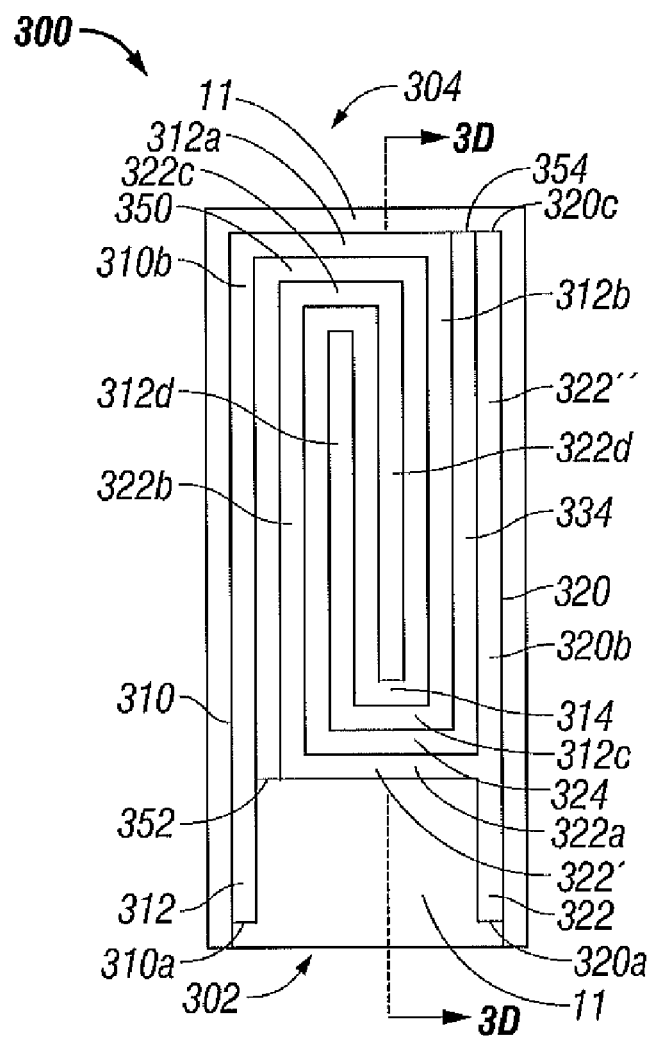
FIG. 3C is a plan view of the bipolar electrode assembly of FIG. 3A illustrating the electrode assembly as disposed at least partially recessed within a substrate.
Figure 3D:
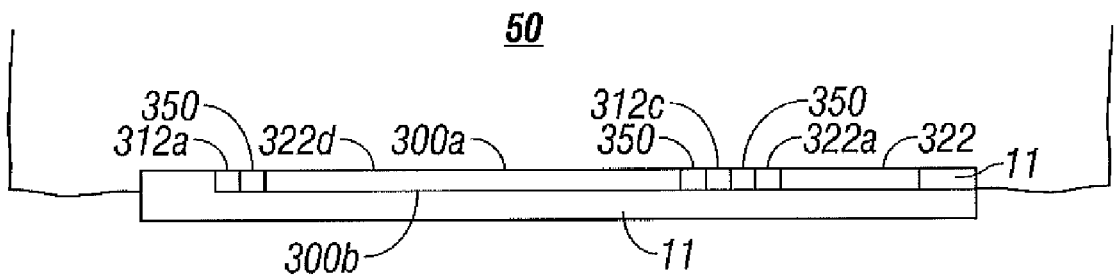
FIG. 3D is a cross-sectional view of the bipolar electrode assembly of FIG. 3C.

FIGS. 3C and 3D illustrate another embodiment of electrode assembly 300 wherein the electrodes 310 and 320 and the cooling medium, e.g., cooling conduit 350, are disposed at least partially recessed within a substrate 11. Those skilled in the art will recognize that, and understand how, the electrode assemblies 100 and 200 described above with respect to FIGS. 1A-1B and 2A-2B, respectively, may also be configured wherein the electrodes 110, 120 and cooling medium, e.g., cooling conduit 150, and the electrodes 210, 220 and cooling medium, e.g., cooling conduit 350, respectively, are disposed at least partially recessed within the substrate 11.

FIGS. 4A, 4B, 5A, 5B, 6A and 6B are exemplary embodiments of bipolar electrode and cooling assemblies that include a plurality of parallel branch electrodes intermittently disposed in electrical isolation one from another, and at least one cooling conduit having a plurality of parallel segments at least partially intermittently disposed in vertical registration with the plurality of parallel branch electrodes.

Figure 4A:
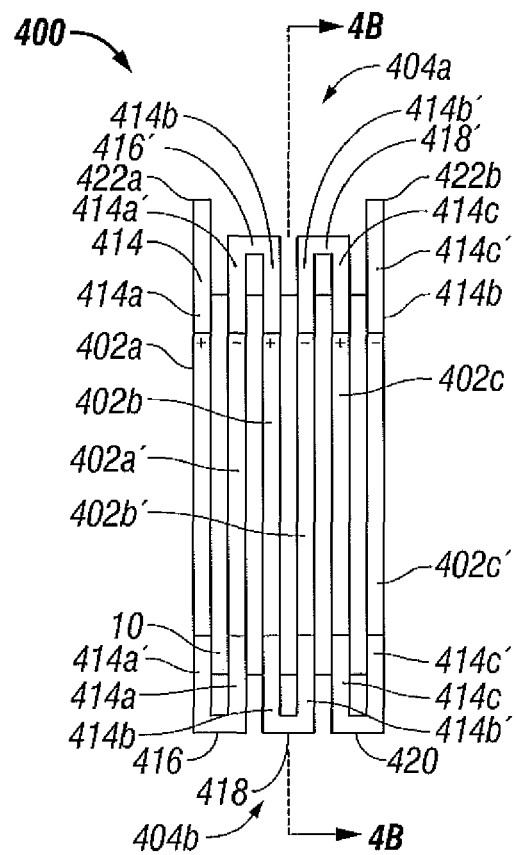
FIG. 4A is a plan view according to the present disclosure of a bipolar electrode assembly having a plurality of parallel branches and having a cooling conduit arranged in a serpentine configuration for serial flow cooling of the bipolar electrode assembly.
Figure 4B:
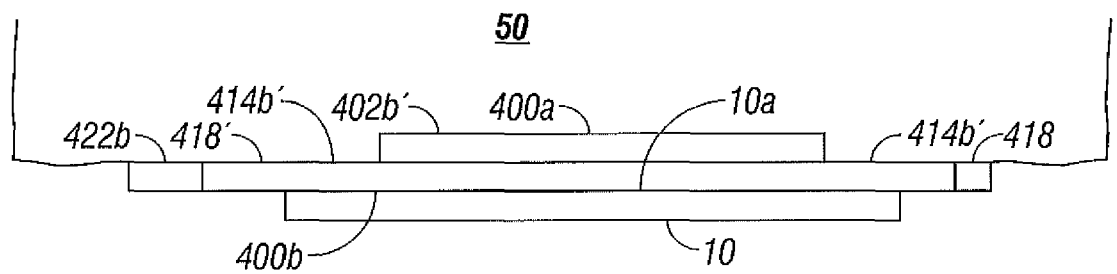
FIG. 4B is a cross-sectional view of the bipolar electrode assembly and cooling conduit of FIG. 4A.

Referring first to FIGS. 4A and 4B, there is illustrated an exemplary embodiment of a bipolar electrode and cooling assembly 400 having a plurality of parallel branch electrodes intermittently disposed in electrical isolation from one another. The electrode and cooling assembly 400 includes a proximal end 404a and a distal end 404b. A first group of the plurality of branch electrodes includes positively charged electrodes 402a, 402c, 402c and a second group of the plurality of branch electrodes includes negatively charged electrodes 402a', 402c', 402c'. The second group of electrodes 402a', 402c', 402c' are intermittently disposed between the first group of electrodes 402a, 402c, 402c with each of the electrodes in electrical isolation one from another.

The electrode assembly 400 also includes at least one cooling conduit 414 having a plurality of parallel segments 414a, 414a', 414b, 414b', 414c, 414c' that are at least partially intermittently disposed in vertical registration with the plurality of parallel branch electrodes 402a, 402c, 402c and 402a', 402c', 402c'. That is, parallel segments 414a, 414b, 414c are in vertical registration with positively charged electrodes 402a, 402c, 402c, respectively, while parallel segments 414a', 414b', 414c' are in vertical registration with negatively charged electrodes 402a', 402c', 402c', respectively. In one embodiment, the cooling conduit 414 is integrally formed with 180 degree loops 416, 416', 418, 418', 420 that join the pairs of parallel segments 414a and 414a'; 414a' and 414b; 414b and 414b'; 414b' and 414c; 414c and 414c', respectively, to form the serpentine configuration of the one or more cooling conduits 414. For the sake of illustration only, the one cooling conduit 414 illustrated in FIGS. 4A and 4B includes at proximal end 404a a cooling inlet port 422a and a cooling outlet port 422c, Thus, the cooling inlet port 422a and the cooling outlet port 422c, as part of the one or more cooling conduits 414 configured in a serpentine configuration, enables serial cooling of the plurality of parallel branch electrodes 402a, 402c, 402c and 402a', 402c', 402c'.

Referring also to FIG. 4B, as described above, parallel segments 414a, 414b, 414c of the one or more cooling conduits 414 are in vertical registration with, and mounted over, positively charged electrodes 402a, 402c, 402c, respectively, while parallel segments 414a', 414b', 414c' are in vertical registration with, and mounted over, negatively charged electrodes 402a', 402c', 402c', respectively. In turn, both the first and second groups of electrodes 402a, 402c, 402c and 402a', 402c', 402c' and the respective parallel segments 414a, 414b, 414c and 414a', 414b', 414c' are mounted over or disposed on a substrate 10 that may be made from a plastic or ceramic such as ABS or zirconia, respectively.

In a similar manner as described above with respect to electrode assemblies 100, 200 and 300, the resulting configuration of the electrode and cooling assembly 400 enables electrode and cooling assembly 400 to be formed in a thin generally rectangular configuration having a first substantially planar side 400a and a second substantially planar side 400b, disposed on the substrate 10 in interfacing relationship therewith, wherein the first substantially planar side 400a is disposed in contact with patient tissue 50 during a surface ablation process.

Figure 5A:
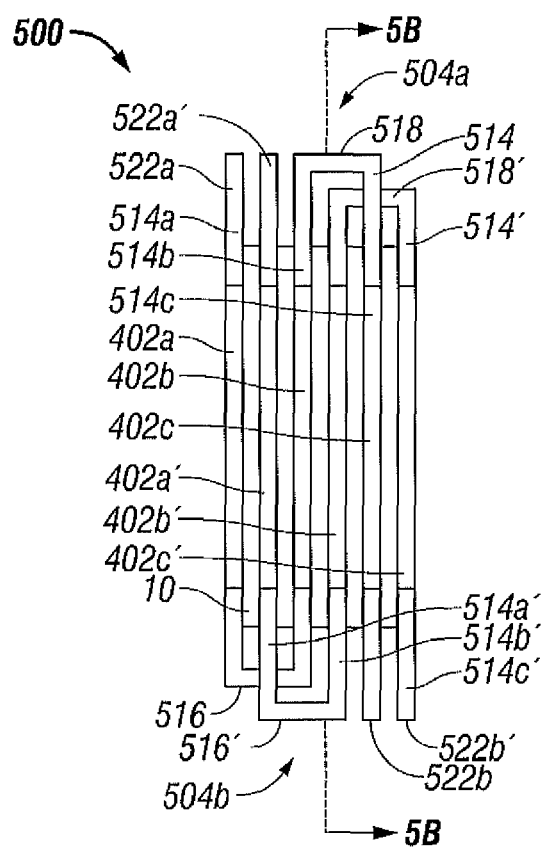
FIG. 5A is a plan view according to the present disclosure of a bipolar electrode assembly having a plurality of parallel branches and having a pair of cooling conduits arranged in an overlapping serpentine configuration each configured for serial flow cooling of the bipolar electrode assembly.
Figure 5B:
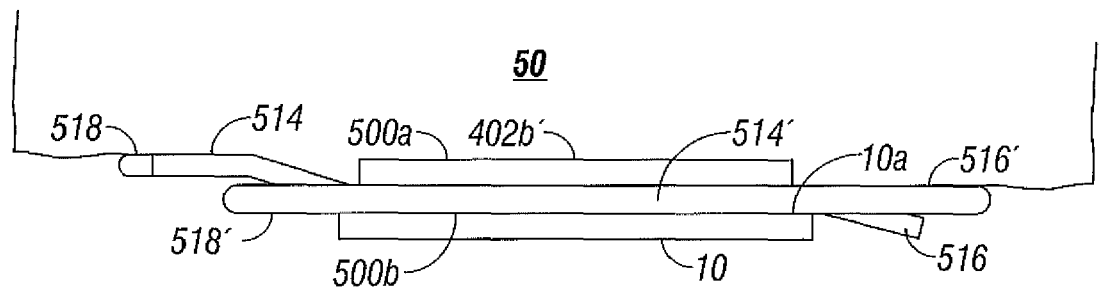
FIG. 5B is a cross-sectional view of the bipolar electrode assembly and cooling conduit of FIG. 5A.

Turning now to FIGS. 5A and 5B, there is illustrated another embodiment of a bipolar electrode and cooling assembly. In the same manner as described above with respect to bipolar electrode and cooling assembly 400, the bipolar electrode and cooling assembly 500 includes the plurality of parallel branch positive and negative bipolar electrodes that are alternately intermittently disposed as first and second groups of electrodes 402a, 402c, 402c and 402a', 402c', 402c', respectively. The bipolar electrode and cooling assembly 500 includes a proximal end 504a and a distal end 504b. However, bipolar electrode and cooling assembly 500 differs from bipolar electrode and cooling assembly 400 in that bipolar electrode and cooling assembly 400 includes first and second cooling conduits 514 and 524, respectively, each configured in a serpentine configuration having a plurality of parallel segments (or legs) 514a, 514b, 514c and 514a', 514b', 514c', respectively.

The plurality of parallel segments 514a, 514b, 514c of the first cooling conduit 514 are intermittently disposed in vertical registration with the plurality of positive parallel branch electrodes 402a, 402c, 402c enabling serial cooling thereof, while the plurality of parallel segments 514a', 514b', 514c' of the second cooling conduit 514' are intermittently disposed in vertical registration with the plurality of negative parallel branch electrodes 402a', 402c', 402c' enabling serial cooling thereof.

In one embodiment, similar to cooling conduit 414, cooling conduit 514 may be integrally formed with 180 degree loops 516, 518 that join the pairs of parallel segments 514a, 514b and 514b, 514c, respectively, while the cooling conduit 514' may be integrally formed with 180 degree loops 516', 518' that join the pairs of parallel segments 514a', 514b'; and 514b', 514c', respectively, to form the serpentine configuration of the first and second cooling conduits 514 and 514', respectively. For the sake of illustration only, cooling conduits 514, 514' illustrated in FIGS. 5A and 5B include at proximal end 504a cooling inlet ports 522a, 522a' and cooling outlet ports 522c, 522c', respectively. Thus, the cooling inlet ports 522a, 522a' and the cooling outlet ports 522c, 522c', as part of the cooling conduits 514, 514', respectively, each configured in a serpentine configuration enable serial cooling of the plurality of parallel branch electrodes 402a, 402c, 402c and 402a', 402c', 402c', respectively. It can be seen also that the first cooling conduit 514 and the second cooling conduit 514' at least partially overlap each other. Specifically, the 180 degree loop 516' of the second cooling conduit 514' overlaps the 180 degree loop 516 of the first cooling conduit 514 while the 180 degree loop 518 of the first cooling conduit 514 overlaps the 180 degree loop 518' of the second cooling conduit 514'.

Referring also to FIG. 5B, in a similar manner as described above, parallel segments 514a, 514b, 514c of the first cooling conduit 514 are in vertical registration with, and mounted over, positively charged electrodes 402a, 402c, 402c, respectively, while parallel segments 514a', 514b', 514c' of the second cooling conduit 514' are in vertical registration with, and mounted over, negatively charged electrodes 402a', 402c', 402c', respectively. In turn, both the first and second groups of electrodes 402a, 402c, 402c and 402a', 402c', 402c' and the respective parallel segments 514a, 514b, 514c and 514a', 514b', 514c' are mounted over or disposed on substrate 10 that may be made from a plastic or ceramic such as ABS or zirconia, respectively.

In a similar manner as described above with respect to electrode and cooling assembly 400, the resulting configuration of the electrode and cooling assembly 500 enables electrode and cooling assembly 500 to be formed in a thin generally rectangular configuration having a first substantially planar side 500a and a second substantially planar side 500b, disposed on the substrate 10 in interfacing relationship therewith, wherein the first substantially planar side 500a is disposed in contact with patient tissue 50 during a surface ablation process.

Figure 6A:
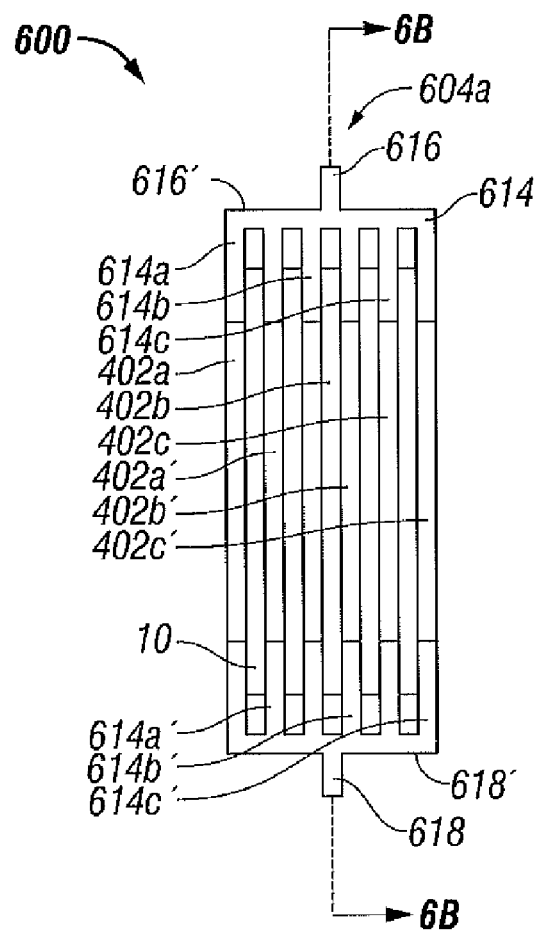
FIG. 6A is a plan view according to the present disclosure of a bipolar electrode assembly having a plurality of parallel branches configured for parallel coolant flow for cooling of the bipolar electrode assembly.
Figure 6B:
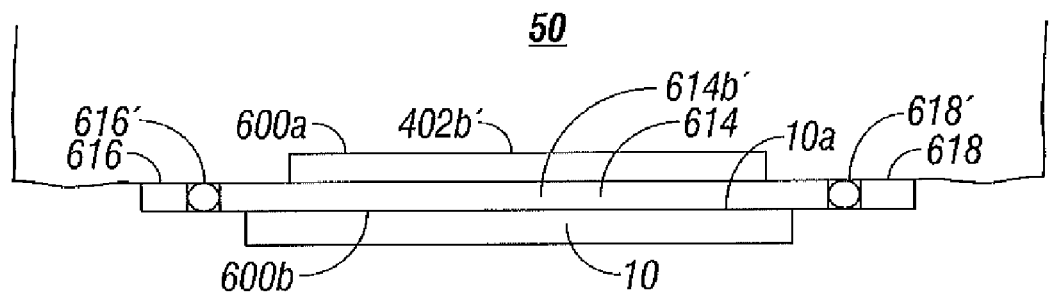
FIG. 6B is a cross-sectional view of the bipolar electrode assembly and cooling conduit of FIG. 6A.
Figure 6C:
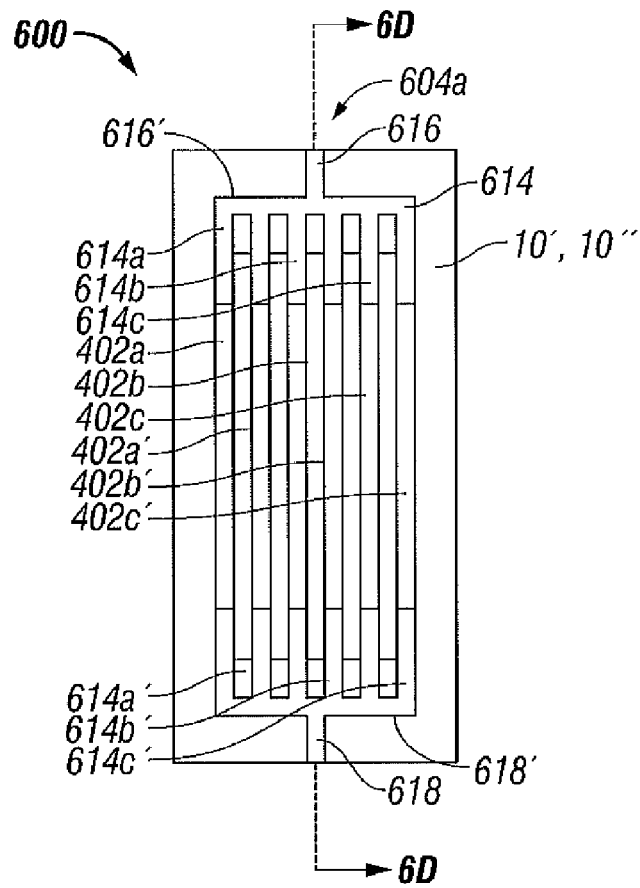
FIG. 6C is a plan view of the bipolar electrode assembly of FIG. 6A illustrating the electrode assembly as disposed at least partially recessed within a substrate.
Figure 6D:
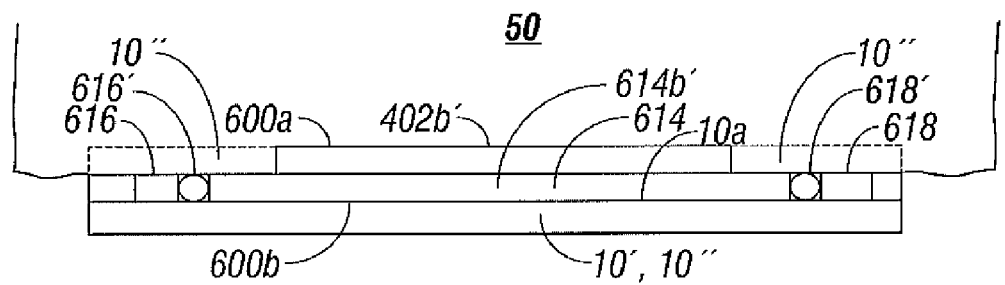
FIG. 6D is a cross-sectional view of the bipolar electrode assembly of FIG. 6C.

Turning now to FIGS. 6A and 6B, there is illustrated one embodiment of a bipolar electrode and cooling assembly that is configured wherein at least one cooling conduit has a common coolant inlet header and a common coolant outlet header enabling parallel cooling of the plurality of branch electrodes. In a similar manner as with respect to bipolar electrode and cooling assemblies 400 and 500 described above, bipolar electrode and cooling assembly 600 includes the plurality of parallel branch positive and negative bipolar electrodes that are alternately intermittently disposed as first and second groups of electrodes 402a, 402c, 402c and 402a', 402c', 402c', respectively. The bipolar electrode and cooling assembly 600 includes a proximal end 604a and a distal end 604b. However, bipolar electrode and cooling assembly 600 differs from bipolar electrode and cooling assemblies 400 and 500 in that bipolar electrode and cooling assembly 600 includes at least one cooling conduit 614 having a plurality of parallel segments 614a, 614b, 614c and 614a', 614b', 614c' that are at least partially intermittently disposed in vertical registration with the plurality of parallel branch electrodes 402a, 402c, 402c and 402a', 402c', 402c', respectively. Additionally, cooling conduit 614 includes a common coolant inlet header 616' and a common coolant outlet header 618' that are each operatively coupled to, or integrally formed with, the plurality of parallel segments 614a, 614b, 614c and 614a', 614b', 614c' to enable parallel cooling of the plurality of branch electrodes 402a, 402c, 402c and 402a', 402c', 402c'. Cooling conduit 614 includes a coolant inlet port 616 and a coolant outlet port 618, each operatively coupled to, or integrally formed with, the plurality of parallel segments 614a, 614b, 614c and 614a', 614b', 614c' to enable parallel cooling of the plurality of branch electrodes 402a, 402c, 402c and 402a', 402c', 402c'.

Referring also to FIG. 6B, in a similar manner as described above with respect to bipolar electrode and cooling assemblies 400 and 500, the parallel segments 614a, 614b, 614c are in vertical registration with, and mounted over, positively charged electrodes 402a, 402c, 402c, respectively, while parallel segments 614a', 614b', 614c' are in vertical registration with, and mounted over, negatively charged electrodes 402a', 402c', 402c', respectively. In turn, both the first and second groups of electrodes 402a, 402c, 402c and 402a', 402c', 402c' and the respective parallel segments 614a, 614b, 614c and 614a', 614b', 614c' are mounted over or disposed on substrate 10 that may be made from a plastic or ceramic such as ABS or zirconia, respectively. The parallel segments for coolant flow enhances the capability of assuring that the positively charged and negatively charged electrodes 402a, 402c, 402c and 402a', 402c', 402c' are approximately the same temperature throughout.

In a similar manner as described above with respect to FIGS. 3C and 3D, FIGS. 6C and 6D illustrate another embodiment of electrode assembly 600 wherein the electrodes 402a, 402c, 402c and 402a', 402c', 402c' and the cooling medium, e.g., cooling conduit 614, are disposed at least partially recessed within a substrate 10' or 10". Substrate 10" differs from substrate 10' in that substrate 10" has a depth sufficient to enable the electrodes 402a, 402c, 402c and 402a', 402c', 402c' to also be disposed at least partially recessed within the substrate 10". Those skilled in the art will also recognize that, and understand how, the electrode assemblies 400 and 500 described above with respect to FIGS. 4A-4B and 5A-5B, respectively, may also be configured wherein the electrodes 402a, 402c, 402c and 402a', 402c', 402c' and cooling medium, e.g., cooling conduits 414 and 514, 514', respectively, are disposed at least partially recessed within the substrate 10' or 10".

Again, in a similar manner as described above with respect to electrode and cooling assemblies 400 and 500, the resulting configuration of the electrode and cooling assembly 600 enables electrode and cooling assembly 600 to be formed in a thin generally rectangular configuration having a first substantially planar side 600a and a second substantially planar side 600b, disposed on the substrate 10 in interfacing relationship therewith, wherein the first substantially planar side 600a is disposed in contact with patient tissue 50 during a surface ablation process.

It can be appreciated from the above description that, referring again to FIGS. 1A, 1B, 2A, 2B, 3A, 3B, the present disclosure relates to a bipolar electrode assembly, e.g., electrode assembly 100, 200 or 300, that includes a substrate 10 having proximal 102, 202, 302 and distal ends 104, 204, 304, respectively, and supporting first electrodes 110, 210, 310 and second electrodes 120, 220, 320, respectively, each adapted to connect, e.g., via the contact extensions 112, 122, 212, 222, 312, 322, respectively, to alternate potentials of an electrosurgical energy source (not shown). The first and second electrodes, e.g., 110, 210, 310 and 120, 220 320, respectively, are disposed in an interwoven configuration across surface 10a of the substrate 10 from the proximal ends 102, 202, 302 to distal ends 104, 204, 304, respectively, thereof, A cooling medium, e.g., cooling conduits 150, 250, 350, is disposed interposed between the first and second electrodes, 110, 210, 310 and 120, 220, 320, respectively, from the proximal ends 102, 202, 302 to distal ends 104, 204, 304, respectively, of the substrate 10. The cooling medium may be disposed at least partially recessed within the substrate (see FIGS. 3C and 3D).

The cooling medium, e.g., water, oil, cooling dielectric, cooling polymer, cooling substrate, etc., may be disposed atop the substrate 10, in interfacing relationship with the second substantially planar side 100b, 200b, 300b, respectively, of the electrode assembly 100, 200, 300.

As illustrated in FIGS. 1A and 1B, the first and second electrodes 110 and 120, respectively, of bipolar electrode assembly 100 each include a plurality of finger-like prongs, e.g., prongs 132, 134, 136, 142, 144, 146 which extend lengthwise along the surface 10a of the substrate 10. The prongs 132, 134, 136 of the first electrode 110 intermesh with the prongs 142, 144, 146 of the second electrode 120 and each prong 132, 134, 136, 142, 144, 146 is separated by a cooling medium as described above, e.g., water, oil, cooling dielectric, cooling polymer, cooling substrate, etc.

As illustrated in FIGS. 2A and 2B, the first and second electrodes 210 and 220, respectively, of bipolar electrode assembly 200 each include a plurality of finger-like prongs, e.g., 214a, 214b, 214c, 214d, 214e and 224a, 224b, 224c, 224d, 224e, respectively, which extend transversely across the surface 10a of the substrate 10 from the proximal end 202 to the distal end 204, thereof, respectively, The prongs 214a through 214e of the first electrode 210 intermesh with the prongs 224a through 224e of the second electrode 220, and each prong 214a through 214e, 224a through 224e, is separated by a cooling medium as described above.

FIGS. 3A and 3B show the first and second electrodes 310 and 320, respectively, of bipolar electrode assembly 300 arranged atop the substrate 10 and extending from the proximal end 302 to distal end 304 of the substrate 10 and spiraling inwardly with the cooling medium disposed therebetween.

As can be appreciated from the foregoing description, as illustrated in FIGS. 1A, 2A and 3A, the cooling medium may be dispersed in a cooling conduit, e.g., cooling conduits 150, 250, 350, disposed in a serpentine configuration in the space formed between the first electrode 110, 210, 310 and the second electrode 120, 220, 320, respectively, e.g., spaces 133, 135 and 143, 145 of electrodes 110, 120; spaces 216ab, 216bc, 216cd, 216de and 226ab, 226bc, 226cd, 226de of electrodes 210, 220; and spaces 314 and 334 of electrodes 310, 320, respectively.

As can also be appreciated from the foregoing description, referring again to FIGS. 4A, 4B, 5A, 5B, 6A, 6B, the present disclosure relates also to a bipolar electrode assembly, e.g., electrode assemblies 400, 500, 600, that include a substrate 10 having proximal ends 402, 502, 602 and distal ends 404, 504, 604, respectively, and supporting a plurality of first electrodes 402a, 402c, 402c and a plurality of second electrodes 402a', 402c', 402c', respectively. Each electrode 402a, 402c, 402c, 402a', 402c', 402c' is adapted to connect to alternate potentials of an electrosurgical energy source (not shown). The plurality of first electrodes 402a, 402c, 402c and second electrodes 402a', 402c', 402c' are disposed in a lengthwise alternating configuration across the surface 10a of the substrate 10. A cooling medium, as described above, e.g., water, oil, cooling dielectric, cooling polymer, cooling substrate, etc., is disposed in vertical registration under each of said plurality of first and second electrodes 402a, 402c, 402c and 402a', 402c', 402c', respectively.

In one embodiment, as illustrated in FIGS. 4A and 4B with respect to bipolar electrode assembly 400, the cooling medium is dispersed in a single conduit 414 which snakes lengthwise across the width of the substrate 10 in vertical registration with each of the plurality of electrodes 402a, 402c, 402c and 402a', 402c', 402c'.

In one embodiment, as illustrated in FIGS. 5A and 5B with respect to bipolar electrode assembly 500, a first cooling medium is dispersed in a first conduit 514 which snakes lengthwise across the width of the substrate 10 in vertical registration with the plurality of first electrodes 402a, 402c, 402c and a second cooling medium is dispersed in a second conduit 524 which snakes lengthwise across the width of the substrate 10 in vertical registration with the plurality of second electrodes 402a', 402c', 402c'. The first conduit 514 and the second conduit 524 may at least partially overlap each other.

In still another embodiment, as illustrated in FIGS. 6A and 6B with respect to bipolar electrode assembly 600, the cooling medium is dispersed in a single conduit 614 which is distributed lengthwise across the width of the substrate 10 in vertical registration with each of the plurality of electrodes 402a, 402a', 402c, 402c', 402c, 402c'.

Those skilled in the art will recognize that the method of using bipolar electrode and cooling assemblies 100, 200, 300, 400, 500, 600 for desiccation of a controlled volume of tissue (surface area time depth) is based on electrode size, spacing, time and energy delivery. Size and spacing of electrodes as well as energy delivery (amplitude, rate, duration, and waveform) determine contact impedance, rate of desiccation and depth of thermal damage. For a given tissue perfusion, controlling the ratio of electrode size versus electrode spacing results in control of the depth of thermal injury. Controlling the area size of the surface desiccation is primarily controlled by the size and shape of the contacting electrodes. A bipolar configuration cooled according to the present disclosure provides more efficient transfer of RF energy, resulting in safe delivery of energy by confining the tissue affect to a region near the active electrodes. Using a feedback control system, the activation time can vary with the surface area and volume of tissue to be treated. For example, 1 millimeter depth may take less than 30 seconds while a 5 millimeter depth may take about three minutes.

The bipolar electrode and cooling assemblies 100, 200, 300, 400, 500, 600 of the present disclosure enable clinical application of contact desiccation to thermally damage tissue with a thickness in the range of about 1 millimeter to about 5 millimeters in depth for a reduction in surface bleeding. Depths in the range of about 5 millimeters to about 10 millimeters may be characteristic of surface ablation to increase clinical margin around a lesion. To effect such surface ablation may require the use of multiple applicators, i.e., bipolar electrode and cooling assemblies, or enabling the user to adjust the size and spacing of the electrodes and cooling assemblies.

The bipolar electrode and cooling assemblies 100, 200, 300, 400, 500, 600 of the present disclosure results in reduced tissue build-up on the electrode and more efficient application of energy. Contact desiccation (surface ablation) of tissue using the bipolar electrode and cooling assemblies of the present disclosure causes minimal adherence of tissue to the electrode surfaces and charring of the electrodes. The interlocking/interwoven electrodes configured with the cooling conduits also configured in an interlocking/interwoven pattern provide intimate contact with the electrodes during the contact desiccation and surface ablation process to maintain a cooler tissue temperature during application of energy as compared to the prior art methods and so allow deeper thermal penetration by minimizing rapid heating and rise of impedance at the electrode to tissue interface. The surface desiccation can be applied over a broad area and an applicator can be configured for precise applications depending on a particular applicator shape as well as electrode size, shape, spacing and energy delivery For example, a curved applicator may be applied to a curved tissue surface and a flat applicator may be applied to a flat tissue surface to cover a broader surface area.

Those skilled in the art will recognize that the bipolar electrode assemblies and electrode and cooling assemblies 100, 200, 300, 400, 500, 600 disclosed herein may be employed as coagulation surfaces of electrosurgical pencils, needle instruments, endoscopic and laparoscopic tissue sealing instruments and the like. Electrode surfaces in contact with patient tissue may include a nickel-based material, coating, stamping, metal injection molding which is designed to reduce adhesion between the jaw members (or components thereof with the surrounding tissue during tissue treatment.

It is also contemplated that the tissue electrode surfaces may be manufactured from one (or a combination of one or more) of the following "non-stick" materials: nickel-chrome, chromium nitride, MedCoat 2000 manufactured by The Electrolizing Corporation of OHIO, Inconel 600 and tin-nickel. For example, high nickel chrome alloys and Ni200, Ni201 (about 100% Ni) may be made into electrode surfaces by metal injection molding, stamping, machining or any like process.

In addition these materials may include an optimal surface energy for eliminating sticking due in part to surface texture and susceptibility to surface breakdown due electrical effects and corrosion in the presence of biologic tissues. These materials exhibit superior non-stick qualities over stainless steel and should be utilized on the instrument in areas where the exposure to pressure and RF energy can create localized "hot spots" more susceptible to tissue adhesion. As can be appreciated, reducing the amount that the tissue "sticks" during ablation improves the overall efficacy of the instrument.

As previously described above, the electrode surfaces may also be "coated" with one or more of the above materials to achieve the same result, i.e., a "non-stick surface". For example, nitride coatings (or one or more of the other above-identified materials) may be deposited as a coating on another base material (metal or nonmetal) using a vapor deposition manufacturing technique.

One particular class of materials disclosed herein has demonstrated superior non-stick properties and, in some instances, superior seal quality. For example, nitride coatings which include, but are not are not limited to: TiN, ZrN, TiAlN, and CrN are preferred materials used for non-stick purposes. CrN has been found to be particularly useful for non-stick purposes due to its overall surface properties and performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having electrodes made from or coated with Ni200, Ni201 (about 100% Ni) also showed improved non-stick performance over typical bipolar stainless steel electrodes.

The non-stick materials may be manufactured from one (or a combination of one or more) of the following "non-stick" materials: nickel-chrome, chromium nitride, MedCoat 2000, Inconel 600, tin-nickel or various nitride coatings which include, but are not limited to, TiN, ZrN, TiAlN and CrN. For example, high nickel chrome alloys, Ni200, Ni201 (~100% Ni) may be made into electrode surfaces by metal injection molding, stamping, machining or any like process. Also and as mentioned above, the electrode surfaces 122 may also be "coated" with one or more of the above materials to achieve the same result, i.e., a "non-stick surface".

Those skilled in the art will also recognize that a cooling mechanism or system that is in fluidic communication with the cooling conduits 150, 250, 350, 414, 514, 614 may include temperature sensors, one or more temperature controllers, at least one cooling mechanism such as a fluid-based heat exchanger using a suitable sterile solution such as water, saline and the like. The cooling mechanism or system may include a fluid pump and tubing in fluidic communication with the tissue-treating electrode assemblies. The cooling mechanism may also include a thermoelectric cooler (TEC) and associated equipment such as fans, power supply, switches, heat sink and the like, for example as described in commonly-owned U.S. Patent Application Publication US 2006/0052778 A1 by Chapman et al., entitled "INCORPORATING RAPID COOLING IN TISSUE FUSION HEATING PROCESSES." The tissue contacting electrodes may be internally cooled or externally cooled. In the case of internally cooled electrodes, the coolant is self-contained in a re-circulating or non-recirculating mode, or the coolant may be made to drip from around the tissue that is in contact with the electrodes. The tissue contacting electrodes may be rigid or flexible. The tissue contacting electrodes may be arranged in a monopolar, bipolar, sesquipolar (one and one half) or omnipolar configuration (i.e., a combination of monopolar and/or bipolar and/or sesquipolar). When sesquipolar electrodes are used, the electrode having a smaller surface area should be cooled to a temperature lower than the temperature of the electrodes having a larger surface area to balance the tissue heating. The electrode surface area size should be balanced with the degree of electrode cooling being applied. For bipolar electrodes, coolant temperature is matched to prevent electrode to electrode temperature gradient mismatch.

The energy source may be a radiofrequency (RF), thermal electric/resistive, frictional (e.g., ultrasound), combustion, radiation (e.g., microwave (MW) frequency), or acoustical (e.g., ultrasound). The application of energy may be feedback controlled by an algorithm that adjusts the energy delivery based on the inputs of electrode type (electrical and mechanical characteristics or properties), coolant properties (flow rate, temperature, distance of coolant path, electrode temperature), energy delivery, intended use, user input, and tissue characteristics. Inputs may be measured, sensed, manually entered, user selected, retrieved from a look-up table or from a data array, or other suitable means. The delivery of energy may be constant, pulsed, or variable with time or with location on the tissue surface.

The electrodes 110, 120; 210, 220; 310, 320; 402a, 402c, 402c and 402a', 402c', 402c' may have a tubular cross-section. The tubular electrodes may be rigid or flexible and may be conductive tubing made from, for example and not limited to, stainless steel with insulated sections to protect tissue that is to be left untreated. Alternatively, the tubular electrodes may be non-conductive tubing made from, for example and not limited to, a polymer material with conductive material configured around the non-conductive tubular member. The conductive material may be conductive foil placed over a tubular electrode, or be a conductive material that is vapor deposited on the tubular electrode. The tubular or rounded electrodes minimize high current densities caused by high e-fields at the sharp electrode edges (i.e., edge effects).

An electrical pulse may be applied to measure tissue properties. The measured tissue properties may include impedance, conductance, voltage to current phase shift, energy pulse and measurement of thermal response related to tissue perfusion, rate of impedance change or other suitable property. Once therapeutic energy has been applied to the tubular electrodes, the status of the treatment is monitored and the treatment is continued, adjusted or halted.

The substrate 10 on which the electrodes 110, 120; 210, 220; 310, 320; 402a, 402c, 402c and 402a', 402c', 402c' are disposed is electrically insulating, i.e., electrically non-conductive, but thermally conductive, and may be made from materials including, but not limited to, thermally conductive plastic materials which dissipate heat along a preferred isothermal profile to the surrounding environment resulting in a lower maximum temperature and reduced formation of hot spots. Examples of such materials are commonly sold under the trademark CoolPoly® by Cool Polymers, Inc., of Warwick, R.I., USA, and composite materials such as $ALO_2$. The substrate 10 is thermally cooled and is in thermal communication with the electrodes, such as by direct contact. The substrate 10 may be thermally cooled by any of the methods previously described, e.g., by thermoelectric cooling (TEC). In one embodiment, the electrodes 110, 120; 210, 220; 310, 320; 402a, 402c, 402c and 402a', 402c', 402c' are configured of thin conductive foil or of a metal layer deposited on an externally cooled non-electrically conductive surface. For example, the substrate 10 may be made from a ceramic material and the electrodes 110, 120; 210, 220; 310, 320; 402a, 402c, 402c and 402a', 402c', 402c' are disposed thereupon such that cooling applied to the substrate externally cools the electrodes which are in contact with the patient tissue. The electrode surface area is matched to ensure proper bipolar electrical conduction. The electrode surface area may be changed in response to the treatment results.

While various embodiments of the disclosure have been described, it is not intended that the disclosure be limited thereto, as it is intended that the disclosure be as broad in scope as the art will allow and that the specification be read likewise. Therefore, the above descriptions should not be construed as limiting, but merely as exemplifications of particular embodiments. Those skilled in the art will envision other modifications within the scope and spirit of the claims appended hereto.

What is claimed is:

1. A bipolar electrode assembly comprising:
    a substrate having proximal and distal ends and supporting first electrode and second electrodes each configured to connect to alternate potentials of an electrosurgical energy source, the substrate made from a rigid, heat-resistant ceramic;
    the first and second electrodes disposed in an interwoven configuration across the surface of the substrate from the proximal to distal ends thereof; and
    a cooling medium interposed between the first and second electrodes from the proximal to distal ends of the substrate,
    wherein the first and second electrodes each include a plurality of finger-like that extend lengthwise along the surface of the substrate, the prongs of the first electrode intermeshing with the prongs of the second electrode, each prong separated by the cooling medium with respect to the substrate.

2. A bipolar electrode assembly according to claim 1, wherein the cooling medium is recessed with the substrate.

3. A bipolar electrode assembly according to claim 1 wherein the cooling medium is disposed atop the substrate.

4. A bipolar electrode assembly according to claim 1 wherein the cooling medium is dispersed through a conduit disposed at least partially recessed within the substrate.

5. A bipolar electrode assembly according to claim 1 wherein the cooling medium is dispersed through a conduit disposed atop the substrate.

6. A bipolar electrode assembly according to claim 1 wherein the cooling medium is selected from the group consisting of saline, water, alcohol, glycine, and oil.

7. A bipolar electrode assembly according to claim 1 wherein the substrate is selected from the group consisting of zirconia and Sialons.

8. A bipolar electrode assembly comprising:
a substrate having proximal and distal ends and supporting a plurality of first electrodes and a plurality of second electrodes, the substrate made from a rigid, heat-resistant ceramic, each plurality of electrodes configured to connect to alternate potentials of an electrosurgical energy source;
the plurality of first and second electrodes disposed in a lengthwise alternating configuration across the surface of the substrate; and
a cooling medium disposed in vertical registration under each of said plurality of first and second electrodes
wherein the cooling medium is dispersed in a single conduit that snakes lengthwise across the width of the substrate in vertical registration with each of the plurality of electrodes.

9. A bipolar electrode assembly comprising:
a substrate having proximal and distal ends and supporting first electrode and second electrodes, each electrode configured to connect to alternate potentials of an electrosurgical energy source, the substrate made from a rigid, heat-resistant ceramic;
the first and second electrodes disposed in an interwoven configuration across the surface of the substrate from the proximal to distal ends thereof; and
a cooling medium interposed between the first and second electrodes from the proximal to distal ends of the substrate,
wherein the first and second electrodes each include a plurality of finger-like prongs that extend transversely across the surface of the substrate from the proximal to distal ends thereof, the prongs of the first electrode intermeshing with the prongs of the second electrode, each prong separated by the cooling medium with respect to the substrate.

10. A bipolar electrode assembly comprising:
a substrate having proximal and distal ends and supporting first and second electrodes, each electrode configured to connect to alternate potentials of an electrosurgical energy source, the substrate made from a rigid, heat-resistant ceramic;
the first and second electrodes interposed in an interwoven configuration across the surface of the substrate from the proximal to distal ends thereof; and
a cooling medium interposed between the first and second electrodes from the proximal to distal ends of the substrate,
wherein the first and second electrodes are arranged atop the substrate to extend from the proximal to distal ends of the substrate and spiral inwardly with the cooling medium disposed therebetween.

11. A bipolar electrode assembly comprising:
a substrate having proximal and distal ends and supporting first electrode and second electrodes, each electrode configured to connect to alternate potentials of an electrosurgical energy source, the substrate made from a rigid, heat-resistant ceramic;
the first and second electrodes disposed in an interwoven configuration across the surface of the substrate from the proximal to distal ends thereof; and
a cooling medium interposed between the first and second electrodes from the proximal to distal ends of the substrate,
wherein the cooling medium is dispersed in a cooling conduit disposed in a serpentine configuration in the space formed between the first and second electrodes.

12. A bipolar electrode assembly comprising:
a substrate having proximal and distal ends and supporting a plurality of first electrodes and a plurality of second electrodes, the substrate made from a rigid, heat-resistant ceramic, each of the plurality of electrodes configured to connect to alternate potentials of an electrosurgical energy source;
the plurality of first and second electrodes disposed in a lengthwise alternating configuration across the surface of the substrate; and
a cooling medium disposed in vertical registration under each of said plurality of first and second electrodes,
wherein a first cooling medium is dispersed in a first conduit that snakes lengthwise across the width of the substrate in vertical registration with the plurality of first electrodes and a second cooling medium is dispersed in a second conduit that snakes lengthwise across the width of the substrate in vertical registration with the plurality of second electrodes.

13. A bipolar electrode and cooling assembly according to claim 12, wherein the first conduit and the second conduit at least partially overlap each other.

14. A bipolar electrode assembly comprising:
a substrate having proximal and distal ends and supporting a plurality of first electrodes and a plurality of second electrodes, the substrate made from a rigid, heat-resistant ceramic, each plurality of electrodes configured to connect to alternate potentials of an electrosurgical energy source;
the plurality of first and second electrodes disposed in a lengthwise, alternating configuration across the surface of the substrate; and
a cooling medium disposed in vertical registration under each of said plurality of first and second electrodes,
wherein the cooling medium is dispersed in a single conduit that is distributed lengthwise across the width of the substrate in vertical registration with each of the plurality of electrodes.

* * * * *